United States Patent [19]

Woo

[11] 4,362,670

[45] Dec. 7, 1982

[54] ALLYLATION OF CARBON COMPOUNDS

[75] Inventor: Edmund P. Woo, Midland, Mich.

[73] Assignee: The Dow Chemical Company, Midland, Mich.

[21] Appl. No.: 297,661

[22] Filed: Sep. 3, 1981

[51] Int. Cl.$^3$ .................. C07C 121/70; C07C 49/203; C07C 69/593; C07C 79/06

[52] U.S. Cl. .......................... 260/465 K; 260/465.9; 560/190; 560/211; 568/314; 568/346; 568/388; 568/943; 585/534

[58] Field of Search .................. 260/465 K, 465.9; 560/190, 211; 568/346, 388, 314, 943; 585/534

[56] References Cited

FOREIGN PATENT DOCUMENTS 13663 7/1980 European Pat. Off. .

OTHER PUBLICATIONS

Tsuji et al., Tetrahedron Letters, 4387 (1965).
Fiaud et al., Tetrahedron Letters, 21, 4437–4440 (1980).
Genêt et al., Tetrahedron Letters, 21, 3183–3186 (1980).
House, Modern Synthetic Reactions, 494, W. A. Benjamin, Inc., Menlo Park, California (1972).
Takahashi et al., Bull. Chem. Soc. Japan, 45, 230 (1972).
K. E. Atkins, Tetrahedron Letters, 43, 3821–3824 (1970).

Primary Examiner—Dolph H. Torrence
Attorney, Agent, or Firm—Douglas N. Deline

[57] ABSTRACT

Carbon acids are allylated by contacting with an allyl carbonate in the presence of a palladium catalyst.

10 Claims, No Drawings

ALLYLATION OF CARBON COMPOUNDS

BACKGROUND OF THE INVENTION

The present invention relates to an improved process for the allylation of carbon acids without the use of base. More particularly, the present invention comprises the reaction of carbon acids with allyl carbonates in the presence of palladium catalysts.

It is already known to form allylic derivatives of carbon acids by contacting the same with allylic alcohols, amines or esters in the presence of homogeneous palladium catalysts. See, K. E. Atkins, *Tetrahedron Letters*, 43, 3821–3824 (1970). While the process has been found suitable for strongly acid compounds such as acetylacetone it has not been found suitable for allylation of less acidic compounds such as dialkyl malonates or phenylacetonitrile. Besides resulting in no or very little conversion of the acid compounds, the reactants reduce the homogeneous catalyst resulting in a metallic precipitate.

An improved process for the allylation of carbon acids which allows for the allylation of relatively weak carbon acids is desired. Further, a process that does not detrimentally affect the catalyst system is desired.

SUMMARY OF THE INVENTION

According to the present invention an improved process for the allylation of carbon acids is provided. The invented process comprises reacting the carbon acid with an allyl carbonate in the presence of a palladium catalyst. The process results in improved reaction times and lowered reaction temperatures compared to previously known processes. Also, the process for the first time allows the artisan to form allyl derivatives of carbon acids that have heretofore not been capable of allylation without the use of strong base.

The invented process provides a useful method for the preparation of substituted carbon acids from base sensitive reactants. Furthermore, the compounds prepared by the present process find use in various applications in industry as monomers capable of polymerization or copolymerization through the ethylenically-unsaturated allyl functionality and as intermediates for preparing herbicides, insecticides and other useful chemicals.

DETAILED DESCRIPTION OF THE INVENTION

The allyl carbonates for use according to the invention are of the formula:

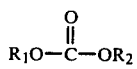

where $R_1$ is

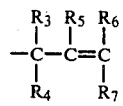

wherein $R_3$–$R_7$ are independently each occurrence hydrogen or a hydrocarbyl radical of up to 20 carbons selected from the group consisting of alkyl, aryl, alkaryl, aralkyl, alkenyl and inertly-substituted derivatives thereof; and $R_2$ is $R_1$ or a hydrocarbyl radical of up to about 20 carbons selected from the group consisting of alkyl, aryl, alkaryl, aralkyl and inertly-substituted derivatives thereof.

By the term "inertly-substituted derivatives" is meant chemical derivatives of the named compounds containing substituents that are unreactive under the reaction conditions and non-interfering with the desired allylation reaction. Suitable inertly-substituted compounds are those compounds that do not contain ionizable carbon-hydrogen bonds. They may be easily identified by routine experimentation. It is already known, for example, that phenol-, carboxy- or amine-containing substituents are unsuitable but that alkoxy, aryloxy, halogen or halogenated alkyl or aryl substituents may be present.

The allyl carbonates for use according to the present invented process are known compounds or else they may be prepared by techniques well-known in the art. Preferred allyl carbonates are those wherein $R_2$ is $C_{1-4}$ alkyl and $R_1$ is allyl or methallyl.

The carbon acids for use according to the invention are those compounds having at least one acidic carbon-hydrogen bond. By the term "acidic" is meant an ionizable hydrogen giving the compound a pK equal to or less than 25. Representative carbon acids include those compounds listed in Table 9-1 of H. O. House, *Modern Synthetic Reactions*, 494, W. A. Benjamin, Inc., Menlo Park, California (1972) which teaching is incorporated herein by reference. Generally, esters, ketones, alkyl cyanides and nitroalkanes having up to about 20 carbons with at least one α-hydrogen may be allylated. Also suitable are compounds of up to about 20 carbons which contain a terminal acetylene moiety.

The palladium catalysts for use according to the invention include both homogeneous and heterogeneous palladium catalysts. Included as representative are stable complexes, such as tetrakis(rtriphenylphosphine) palladium (O), and other homogeneous complexes of palladium or palladium complexed with a polymeric ligand, such as a functionalized styrene divinylbenzene copolymer wherein the functional groups are capable of forming complexes. Suitable functional groups include trialkyl or triaryl phosphines. Also included are salts, such as palladium acetate and heterogeneous palladium catalysts, such as palladium itself or more preferably palladium deposited onto an inert support, such as carbon, diatomaceous earth, silica, alumina, zeolites, etc. Beneficially, a small amount of a complexing agent, such as a phosphine, phosphite or arsine is added to the reaction mixture when the palladium salts or solid palladium catalysts are employed. Preferably, the amount of such complexing agent added will be from about 0.5 to 4 equivalents per equivalent of palladium catalyst based on the stoichiometry of the complex formed.

According to the invention, the allyl carbonate, carbon acid and a catalytic amount of the palladium catalyst are contacted under an inert atmosphere until the evolution of carbon dioxide ceases. The product may be then recovered by distillation.

The temperature of the reaction may be from about −20° C. to about 150° C. and preferably is from about 20° C. to about 100° C. Reduced or elevated pressures may be employed if desired but no advantage generally results thereby. Preferred is to employ atmospheric pressure and ordinary glass or glass-lined reactor vessels. Reaction times from 0.1 hour to 100 hours may be required depending on the reactants and the reaction conditions employed.

The presence of a solvent is not essential to the reaction but a solvent may be employed if desired to aid in temperature control and in the efficient mixing and contacting of reactants. Ethereal solvents, such as alkyl ethers, polyoxyalkylene ethers and tetrahydrofuran may be used. Other suitable solvents, depending on the nature of the reactants, include aromatic hydrocarbons, ketones, esters, alkyl carbonates, cyanoalkanes, alkanols and chlorinated hydrocarbons.

The amount of catalyst employed is generally from about 0.1 to about 10 percent by weight palladium, preferably from about 0.1 to about 2 percent.

results along with the reaction conditions employed are contained in Table I.

TABLE I

| Example | Carbon Acid | Allylating Agent | Catalyst | % Conversion Carbon Acid | % Conversion Allylating Agent | % Yield Monoallylated Product | Reaction Conditions Temp °C. | Reaction Conditions Time (hr) |
|---|---|---|---|---|---|---|---|---|
| 2 | diethylmalonate | allyl alcohol | Pd(AcAc)$_2$[1] | 2 | 68.6[2] | 2.0 | 85 | 3.0 |
| 3 | phenylacetonitrile | allyl alcohol | Pd(OAc)$_2$[3] | 0 | 43.5[2] | 0 | 80 | 3.0 |
| 4 | diethylmalonate | methyl allyl carbonate | Pd(AcAc)$_2$[1] | 66 | 80.0 | 64.0 | 22 | 3.0 |
| 5 | diethylmalonate | ethyl allyl carbonate | Pd(OAc)$_2$[3] | 85 | 93.0 | 81.3 | 22 | 6.6 |
| 6 | phenylacetonitrile | methyl allyl[4] carbonate | Pd(OAc)$_2$[3] | — | — | 51.8 | 80 | 2.0 |

[1] 0.5 Mole percent palladium acetylacetone, 1.5 mole percent triphenylphosphine.
[2] The palladium chelate was destroyed resulting in metal precipitation.
[3] 0.5 Mole percent palladium acetate, 1.5 mole percent triphenylphosphine.
[4] Methylallyl carbonate was added to the reaction flask employed in Example 3 and the contents reheated; no additional catalyst was added.

SPECIFIC EMBODIMENTS

Having described my invention, the following examples are provided as further illustrative and are not to be construed as limiting.

EXAMPLE 1

In a glass flask, diethyl malonate (3.2 g, 0.020 mole), allyl ethyl carbonate (2.6 g, 0.020 mole), tetrahydrofuran (50 ml) and tetrakis(triphenylphosphine) palladium (O) (0.51 g, 0.032 mmole) were combined with stirring under a nitrogen atmosphere at room temperature. After five minutes a sample of the reaction was removed and analyzed by gas-liquid chromatography. The analysis detected less than 1 percent of either starting reactant. Vacuum distillation gave 3.74 g (94 percent yield) of a clear liquid identified as diethyl allylmalonate with less than 1 percent of diethyl diallylmalonate.

EXAMPLES 2–6

Under reaction conditions similar to those of Example 1, the process of the present invention was compared with prior art process using allyl alcohol as the allylating agent. The carbon acids employed with diethyl malonate and phenylacetonitrile. Even employing longer reaction times and elevated temperatures, the conversions and yields of monoallylated product employing the prior art allylating agent, allyl alcohol, in Examples 2 and 3 were drastically inferior to those obtained using allyl carbonate according to the invention. Furthermore, competing side reactions in Examples 2 and 3 caused the formation of large amounts of undesired by-products and converted the homogeneous palladium catalyst to the much less active elemental state in the form of a palladium mirror. Comparative

EXAMPLES 7–8

The reaction conditions of Example 1 were again substantially repeated comparing methylallyl carbonate with allyl alcohol in the allylation of acetylacetone. The catalyst was 0.5 mole percent palladium acetylacetone/1.5 mole percent triphenylphosphine. Results and reaction conditions are contained in Table II.

TABLE II

| Example | Allylating Agent | Conversion (%) Allylating Agent | Conversion (%) Acetylacetone | Yield (%) Mono Allyl | Yield (%) Di Allyl | Temp (°C.) | Time (hr) |
|---|---|---|---|---|---|---|---|
| 7 | allyl alcohol | 98.5 | 91 | 60.0 | 15.6 | 85 | 2.75 |
| 8 | methyl allyl carbonate | 98.0 | 84 | 40.8 | 26.8 | 22 | 2.75 |

It is seen that methylallyl carbonate is a significantly improved allylating agent compared to allyl alcohol inasmuch as lower reaction temperatures were employed for the reaction yet similar results were obtained. In fact larger amounts of the dialkylated reaction product were produced employing methylallyl carbonate even at the lower reaction conditions employed.

EXAMPLE 9

The reaction conditions of Example 1 were substantially repeated. The reactants were ethyl methylallyl carbonate (2.88 g, 0.020 mole), diethyl ethylmalonate (3.76 g, 0.020 mole) in tetrahydrofuran solvent. The catalyst was palladium acetate (0.010 g, 0.045 mmole) complexed with triphenylphosphine (0.10 g, 0.38 mmole), After refluxing for 10 hours under nitrogen atmosphere, analysis by gas-liquid chromatography showed 98.4 percent yield of the desired diethyl methallylethylmalonate.

EXAMPLE 10

To a mixture of ethyl methallyl carbonate (2.88 g, 0.020 mole), diethyl ethylmalonate (3.76 g, 0.020 mole) and triphenylphosphine (0.10 g, 0.38 mmole) in tetrahydrofuran (40 ml) was added palladium acetate (0.010 g, 0.045 mmole). The mixture was refluxed for 10 hours under N₂. Gas chromatographic analysis showed 94.8 percent yield of the desired diethyl methallylethylmalonate.

EXAMPLE 11

A mixture of ethyl methallyl carbonate (0.72 g, 5 mmole), diethyl malonate (0.80 g, 5 mmole), triphenylphosphine (0.28 g, 1.06 mmole), 5 percent palladium on charcoal (0.75 g) and tetrahydrofuran (15 ml) was refluxed under N₂ for 2.5 hours. Analysis of the mixture indicated the reaction was essentially complete. The catalyst was recovered by filtration and was repeatedly washed with diethyl ether.

The recovered catalyst was added to another tetrahydrofuran solution containing the same amounts of ethyl methallyl carbonate and diethyl malonate but only 0.20 g (2.076 mmoles) of triphenylphosphine, and the resulting mixture refluxed for 1.5 hours. The catalyst was again recovered. The two product solutions were combined and subjected to distillation. The distillate (2.08 g, 97 percent) consisted of 5.3 percent of unreacted diethyl malonate, 89.2 percent of diethyl allylmalonate, 4.6 percent of diethyl diallylmalonate, and two other unidentified minor components totalling 1.2 percent.

EXAMPLE 12

The catalyst recovered from Example 11 was added to a solution of phenylacetonitrile (1.172 g, 0.010 mole), ethyl methallyl carbonate (1.445 g, 0.010 mole), triphenylphosphine (0.14 g, 0.53 mmole) in tetrahydrofuran (10 ml). After refluxing for 3 hours under N₂, all the ethyl methallyl carbonate had been consumed. Gas chromatographic analysis of the mixture using p-diisopropylbenzene as standard showed the following composition: unreacted phenylacetonitrile, 2.56 mmoles; methallylphenylacetonitrile, 5.50 mmoles; dimethallylphenylacetonitrile, 1.83 mmoles. Thus the yields of monoallylated and diallylated products were 73.9 percent and 24.6 percent, respectively, based on consumed phenylacetonitrile.

EXAMPLE 13

A mixture of ethyl methallyl carbonate (1.58 g, 0.011 mole), phenylacetylene (1.02 g, 0.010 mole) and tetrakis(triphenylphosphine) palladium (O) (0.25 g, 0.21 mmole) in tetrahydrofuran (15 ml) was refluxed for 91 hours under N₂. Gas chromatographic analysis showed that the ethyl methallyl carbonate was totally consumed but about 10 percent of phenylacetylene remained. The product, methallylphenylacetylene, was isolated by preparative gas chromatography (0.96 g, 61.5 percent yield) and identified by spectroscopic techniques.

EXAMPLE 14

A mixture of ethyl methallyl carbonate (2.88 g, 0.020 mole), pentane-2,4-dione (2.00 g, 0.020 mole), tetrakis(triphenylphosphine) palladium (O) (0.069 g, 0.06 mmole), p-diisopropylbenzene (0.40 g as internal standard), in tetrahydrofuran (10 ml) was stirred at room temperature under N₂ for 1.5 hours. Gas chromtographic analysis showed the following composition: unreacted pentane-2,4-dione, 27.3 percent; 3-methallylpentane-2,4-dione, 48.6 percent; 3,3-dimethallylpentane-2,4-dione, 24.3 percent.

EXAMPLE 15

A mixture containing ethyl methallyl carbonate (1.44 g, 0.010 mole), cyclohexanone (0.98 g, 0.010 mole), 5 percent palladium on carbon (1.0 g), triphenylphosphine (0.20 g, 0.76 mmole), and tetrahyrofuran (15 ml) was refluxed under N₂ for 22 hours. Gas chromatographic quantification by means of an internal standard (ethylbenzene) showed 41.6 percent of the cyclohexanone has been consumed and that the desired product, 2-methallylcyclohexanone was formed in 49.2 yield based on unrecovered cyclohexanone. Preparative gas chromatography of the crude mixture gave a pure sample of the product whose structure was confirmed by infrared and nuclear magnetic resonance spectroscopy.

What is claimed is:

1. A process for allylating a carbon acid comprising reacting the carbon acid with allyl carbonate in the presence of a palladium catalyst.

2. The process of claim 1 wherein the allyl carbonate is of the formula

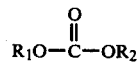

where $R_1$ is

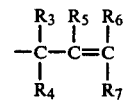

wherein $R_3$–$R_7$ are independently each occurrence hydrogen or a hydrocarbyl radical of up to about 20 carbons selected from the group consisting of alkyl, aryl, alkaryl, aralkyl, alkenyl and inertly-substituted derivatives thereof; and $R_2$ is $R_1$ or a hydrocarbyl radical of up to about 20 carbons selected from the group consisting of alkyl, aryl, alkaryl, aralkyl and inertly-substituted derivatives thereof.

3. The process of claim 2 wherein $R_2$ is $C_{1-4}$ alkyl and $R_1$ is allyl or methallyl.

4. The process of claim 1 wherein the carbon acid is a compound containing an ionizable carbon-hydrogen bond such that the pK of the compund is equal to or less than 25.

5. The process of claim 1 wherein the carbon acid is a compound of up to about 20 carbons selected from the group consisting of α-hydrogen-containing esters, ketones, alkyl cyanides and nitroalkanes and compounds containing terminal acetylene functionality.

6. The process of claim 1 wherein the palladium catalyst is selected from the group consisting of stable homogeneous complexes of palladium, palladium complexed with polymeric ligands, palladium salts and heterogeneous palladium catalysts.

7. The process of claim 1 wherein the allylation is conducted at a temperature from about −20° C. to about 150° C.

8. The process of claim 7 wherein the allylation is conducted at a temperature from about 20° C. to about 100° C.

9. The process of claim 1 wherein a solvent is also present.

10. The process of claim 9 wherein the solvent is selected from the group consisting of ethers, aromatic hydrocarbons, ketones, esters, alkyl carbonates, cyanoalkanes, alkanols and chlorinated hydrocarbons.

* * * * *